US006496711B1

(12) United States Patent
Athan et al.

(10) Patent No.: US 6,496,711 B1
(45) Date of Patent: *Dec. 17, 2002

(54) PULSE OXIMETER PROBE

(75) Inventors: Stephan Peter Athan, Tampa, FL (US); John Edward Scharf, Oldsmar, FL (US)

(73) Assignee: University of Florida, Tampa, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/476,538

(22) Filed: Jan. 3, 2000

Related U.S. Application Data

(63) Continuation of application No. 08/751,645, filed on Nov. 18, 1996, now Pat. No. 6,011,985, which is a continuation of application No. 08/221,958, filed on Apr. 1, 1994, now Pat. No. 5,575,284.

(51) Int. Cl.$^7$ .................................................. A61B 5/00
(52) U.S. Cl. ......................... 600/323; 600/322; 600/324
(58) Field of Search ................................. 600/310, 322, 600/323, 324, 473, 476, 479; 128/903; 356/41; 250/214 A, 214 L

(56) References Cited

U.S. PATENT DOCUMENTS

| | | |
|---|---|---|
| 3,802,776 A | 4/1974 | Tchang |
| 3,815,583 A | 6/1974 | Scheidt |
| 4,109,643 A | 8/1978 | Bond et al. |
| 4,167,331 A | 9/1979 | Nielsen |
| 4,266,554 A | 5/1981 | Hamaguri |

(List continued on next page.)

FOREIGN PATENT DOCUMENTS

| | | |
|---|---|---|
| SU | 1377605 | 2/1986 |
| WO | 92/07505 | 10/1990 |

OTHER PUBLICATIONS

"Optimization of Portable Pulse Oximetry Through Fourier Analysis" Scharf, et al., IEEE, 6/93, pp. 233–235, first available on Apr. 2, 1993, at the IEEE, 12th Southern Biomedical Conference at Tulane University, New Orleans, LA, held Apr. 2, 1993–Apr. 4, 1993.
"Pulse Oximetry Through Spectral Analysis" by Scharf, et al., 1993 IEEE, 6/93, pp. 227–229, first available on Apr. 2, 1993, at the IEEE, 12th Southern Biomedical Conference at Tulane University, New Orleans, LA, held Apr. 2, 1993–Apr. 4, 1993.
"Direct Digital Capture of Pulse Oximetry Waveforms" by Scharf, et al., 1993 IEEE, 6/93, pp. 230–232, first available on Apr. 2, 1993 at the IEEE, 12th Southern Biomedical Conference at Tulane University, New Orleans, LA, held Apr. 2, 1993–Apr. 4, 1993.
Light–To–Frequency Converter—TSL220, Texas Instruments Inc., D3619, 8/90, Rev. 6/91.
Programmable Light–To–Frequency Converter—TSL230, Texas Instruments Inc., SOES007A, 12/92, Rev. 12/9.
CMOS—8–Bit Buffered Multiplying DAC—AD7524, Digital–to–Analog Converters, Rev. A, pp. 2–399, 402–403.
Burr–Brown ACF2101 Advertisement and Product Data Sheet (PDS–1079, 3/91).
"In Vivo Reflectance of Blood and Tissue as a Function of Light Wavelength", Cui, et al., IEEE Transactions on Biomedical Engineering, vol. 37, No. 6, p632–639, Jun. 1990.

*Primary Examiner*—Eric F. Winakur
(74) *Attorney, Agent, or Firm*—Thelen Reid & Priest LLP; David B. Ritchie

(57) ABSTRACT

A diagnostic instrument for determining a cardiovascular system parameter. In one embodiment, the instrument takes the form of a portable pulse oximeter comprising a light to frequency converter (LFC) as a sensor. Also provided is a light to frequency converter comprising a photoresistor and capacitor in circuit communication with an inverting Schmitt trigger and configured such that the inverter generates a periodic electrical signal corresponding to the amount of electromagnetic radiation illuminating the photoresistor.

26 Claims, 6 Drawing Sheets

U.S. PATENT DOCUMENTS

| | | |
|---|---|---|
| 4,267,844 A | 5/1981 | Yamanishi |
| 4,357,105 A | 11/1982 | Loretz |
| 4,407,290 A | 10/1983 | Wilber |
| 4,447,150 A | 5/1984 | Heinemann |
| 4,498,020 A | 2/1985 | Glolma et al. |
| 4,586,513 A | 5/1986 | Hamaguri |
| 4,694,833 A | 9/1987 | Hamaguri |
| 4,800,495 A | 1/1989 | Smith |
| 4,807,630 A | 2/1989 | Malinouskas |
| 4,807,631 A | 2/1989 | Hersh et al. |
| 4,824,242 A | 4/1989 | Frick et al. |
| 4,869,254 A | 9/1989 | Stone et al. |
| 4,883,353 A | 11/1989 | Hausman et al. |
| 4,911,167 A | 3/1990 | Corenman et al. |
| 4,934,372 A | 6/1990 | Corenman et al. |
| 4,997,769 A | 3/1991 | Lundsgaard |
| 5,040,539 A | 8/1991 | Schmitt et al. |
| 5,047,208 A | 9/1991 | Schweitzer et al. |
| 5,078,136 A | 1/1992 | Stone et al. |
| 5,111,817 A | 5/1992 | Clark et al. |
| 5,113,861 A | 5/1992 | Rother |
| 5,149,503 A | 9/1992 | Kohno et al. |
| 5,167,230 A | 12/1992 | Chance |
| 5,190,038 A | 3/1993 | Polson et al. |
| 5,299,570 A | 4/1994 | Hatschek |
| 5,300,769 A * | 4/1994 | Dahlin et al. .................. 356/41 |
| 5,308,919 A | 5/1994 | Minnich |
| 5,365,924 A | 11/1994 | Erdman |
| 5,524,617 A | 6/1996 | Mannheimer |
| 5,575,284 A | 11/1996 | Athan et al. |
| 6,011,985 A * | 1/2000 | Athan et al. ................. 600/322 |

\* cited by examiner

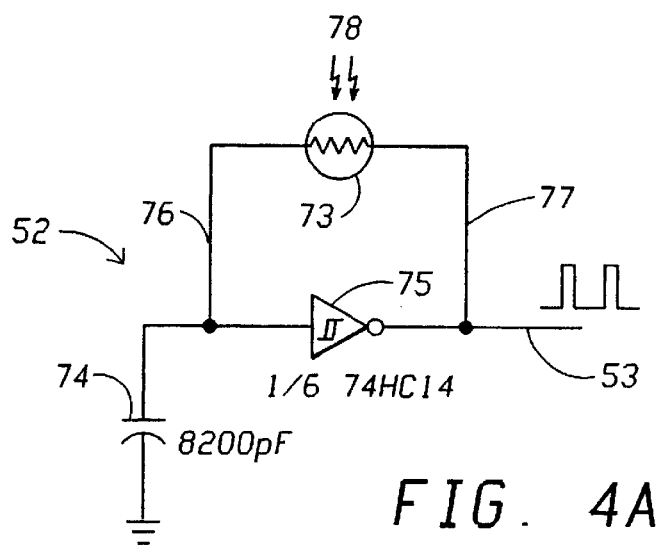
FIG. 4A
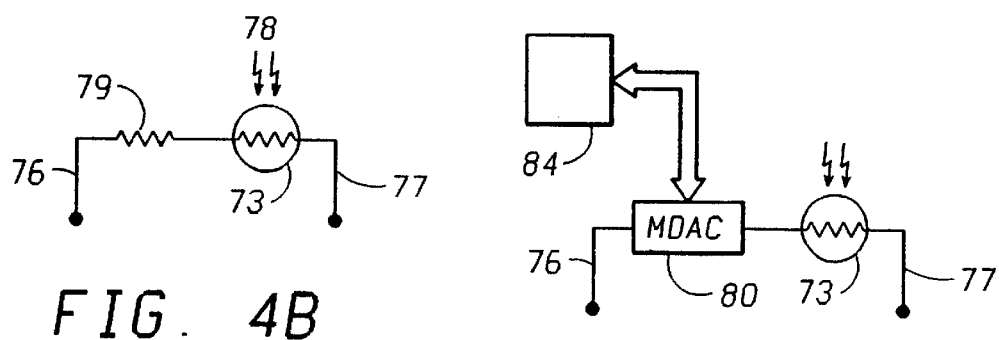
FIG. 4B
FIG. 4C
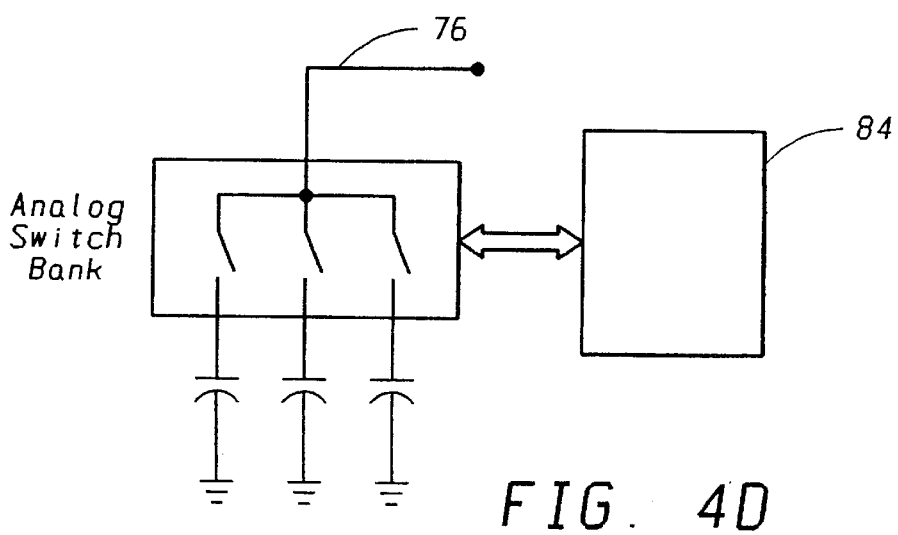
FIG. 4D

PULSE OXIMETER PROBE

This is a continuation of application Ser. No. 08/751,645, filed Nov. 18, 1996, now U.S. Pat. No. 6,011,985 which is a continuation of application Ser. No. 08/221,958, filed Apr. 1, 1994, now U.S. Pat. No. 5,575,284.

FIELD OF THE INVENTION

The present invention relates generally to medical diagnostic instruments and, more specifically, to a portable pulse oximeter with a remote light-to-frequency converter as a sensor and a telemetry system to telemeter the calculated saturation value to a remote display.

BACKGROUND OF THE INVENTION

The degree of oxygen saturation of hemoglobin, $SpO_2$, in arterial blood is often a vital index of the condition of a patient. As blood is pulsed through the lungs by the heart action, a certain percentage of the deoxyhemoglobin, RHb, picks up oxygen so as to become oxyhemoglobin, $HbO_2$. From the lungs, the blood passes through the arterial system until it reaches the capillaries at which point a portion of the $HbO_2$ gives up its oxygen to support the life processes in adjacent cells.

By medical definition, the oxygen saturation level is the percentage of $HbO_2$ over the total hemoglobin; therefore, $SpO_2=HbO_2/(RHb+HbO_2)$. The saturation value is a very important physiological value. A healthy, conscious person will have an oxygen saturation of approximately 96 to 98%. A person can lose consciousness or suffer permanent brain damage if that person's oxygen saturation value falls to very low levels for extended periods of time. Because of the importance of the oxygen saturation value, "Pulse oximetry has been recommended as a standard of care for every general anesthetic." Kevin K. Tremper & Steven J. Barker, *Pulse Oximetry,* Anesthesiology, January 1989, at 98.

An oximeter determines the saturation value by analyzing the change in color of the blood. When radiant energy passes through a liquid, certain wavelengths may be selectively absorbed by particles which are dissolved therein. For a given path length that the light traverses through the liquid, Beer's law (the Beer-Lambert or Bouguer-Beer relation) indicates that the relative reduction in radiation power (P/Po) at a given wavelength is an inverse logarithmic function of the concentration of the solute in the liquid that absorbs that wavelength.

For a solution of oxygenated human hemoglobin, the absorption maximum is at a wavelength of about 640 nanometers (red), therefore, instruments that measure absorption at this wavelength are capable of delivering clinically useful information as to oxyhemoglobin levels.

In general, methods for noninvasively measuring oxygen saturation in arterial blood utilize the relative difference between the electromagnetic radiation absorption coefficient of deoxyhemoglobin, RHb, and that of oxyhemoglobin, $HbO_2$. The electromagnetic radiation absorption coefficients of RHb and $HbO_2$ are characteristically tied to the wavelength of the electromagnetic radiation traveling through them.

It is well known that deoxyhemoglobin molecules absorb more red light than oxyhemoglobin molecules, and that absorption of infrared electromagnetic radiation is not affected by the presence of oxygen in the hemoglobin molecules. Thus, both RHb and $HbO_2$ absorb electromagnetic radiation having a wavelength in the infrared (IR) region to approximately the same degree; however, in the visible region, the light absorption coefficient for RHb is quite different from the light absorption coefficient of $HbO_2$ because $HbO_2$ absorbs significantly more light in the visible spectrum than RHb.

In practice of the pulse oximetry technique, the oxygen saturation of hemoglobin in intravascular blood is determined by (1) alternatively illuminating a volume of intravascular blood with electromagnetic radiation of two or more selected wavelengths, e.g., a red wavelength and an infrared wavelength, (2) detecting the time-varying electromagnetic radiation intensity transmitted through or reflected back by the intravascular blood for each of the wavelengths, and (3) calculating oxygen saturation values for the patient's blood by applying the Lambert-Beer's transmittance law to the detected transmitted or reflected electromagnetic radiation intensities at the selected wavelengths.

Whereas apparatus is available for making accurate measurements on a sample of blood in a cuvette, it is not always possible or desirable to withdraw blood from a patient, and it obviously impracticable to do so when continuous monitoring is required, such as while the patient is in surgery. Therefore, much effort has been expanded in devising an instrument for making the measurement by noninvasive means.

The pulse oximeters used today are desk-top models or handheld models that are interfaced to the patient through the use of a multi-wire bundle. Despite their size and level of technology, these units are still bound by several limitations.

A critical limitation is that of measurement accuracy. In pulse oximetry, signal artifact from patient-probe motion, ambient light, and low perfusion (low blood circulation through the extremities) is one of the primary causes of inaccurate saturation readings. ("Artifact" is any component of a signal that is extraneous to variable represented by the signal.) Inaccuracies are also caused from physiologic non-linearities and the heuristic methods used to arrive at the final saturation values.

Another important limitation is patient confinement to the pulse oximeter, due to the wired probe connecting the patient to the unit. This limits patient mobility in every application of its use, including the emergency room, operating room, intensive care unit, and patient ward.

Thus, three problems plague pulse oximetry. The first problem relates to signal artifact management and inaccuracies of the saturation values due to the non-linear nature of the sample tissue bed. The second problem relates to noise from signal artifact which introduces further inaccuracies. The third problem relates to restricted patient mobility and probe placement due to the wire bundle that physically couples the patient to the oximeter unit and the exclusive use of transmittance-type probes.

Due to the non-linear nature of human physiology, engineers were forced to employ techniques for calculating the final saturation value based not on an analytic solution, but rather, on a calibration curve or look-up table derived from empirical data. This is data that has been collected over hundreds or possibly thousands of patients and stored as a look-up table in the system memory. This technique leads to obvious inaccuracies in the final saturation value since the $SpO_2$ value in the look-up table is only as accurate as the calibration curve programmed into the system memory, which in turn is only as accurate as the in vitro laboratory oximeter used to generate it. These inaccuracies are compounded by differences in skin characteristics between patients, as well as differences over the skin surface of the same patient.

Signal artifact has three major sources: (1) ambient light (which causes an AC/DC masking signal), (2) low perfusion (in which the intensity of the desired AC/DC signal is very low thereby allowing other artifact sources to mask the desired signal more easily), and (3) patient or sensor motion (which generates a large AC/DC artifact masking the desired signal). When the oximetry signal is amplified, the noise components are amplified along with the desired signal. This noise acts to corrupt the primary signal, during both pre-processing as well as post-processing, thereby reducing the accuracy of the pulse oximeter reading. Signal artifact is prevalent with both reflectance- and transmittance-type probes.

Restricted patient mobility is due to the hard wired interface that links the patient probe to the large, bulky oximeter unit. This link is a multi-wire bundle that is used to provide an electrical path for the LED drivers and the photodiode located at the end of the wire bundle in the probe. Probes employing transmittance-type method are restricted to the ears, fingers, or toes and, thus, require physical access to these areas exclusively.

Oximeters are large because of the circuitry heretofore believed necessary to capture the signals and because such higher-powered circuitry shortens battery life. Typical digital oximeters use a silicon photodiode, a current-to-voltage converter (a transimpedance amplifier), a preamplifier, filter stage, a sample and hold, and an analog-to-digital (A/D) converter to capture the oximetry signal. These components make the creation of truly portable oximeters difficult because of the large footprint and high power requirements of each device. The A/D converter, in particular, is typically large and power-hungry.

SUMMARY OF THE INVENTION

According to the present invention, an oximeter is provided with a light-to-frequency converter as a sensor and a telemetry system to telemeter the calculated saturation value to a remote station. The light-to-frequency converter eliminates the need for a separate photodiode, a current-to-voltage converter, a preamplifier, a filter, a sample and hold, and an analog-to-digital (A/D) converter found in typical digital oximeters, thereby significantly reducing the circuit footprint and power consumption. In short, the light-to-frequency converter can be directly connected to an input of a microcontroller or other CPU. The use of telemetry allows accurate hemoglobin saturation level determination to be made without the patient being tethered by a wire bundle to a remote display. Powerful portable systems can be realized using very large-scale integrated circuit (VLSI) multichip module (MCM) technology.

An oximeter made under the present invention is a truly portable unit, capable of capturing and processing oximetry data in a very small package and transmitting calculated saturation values to a remote receiver. The type of receiver that is particularly useful in the context of the present invention is a caregiver's wrist receiver or other type of receiver that communicates to a primary caregiver. In addition, this invention can communicate with other types of receivers, such as a nurses' station receiver or some other personal data receiver. Spread spectrum communication techniques allow highly secure and noise-immune telemetry of saturation values in noisy clinical and healthcare environments.

The oximeter of the present invention uses a pair of light emitting diodes, a light-to-frequency converter, a high-speed counter, a computer system, and an display or other output.

According to the present invention, two light emitting diodes (LEDs), a red LED and an infrared LED, alternatively illuminate an intravascular blood sample with two wavelengths of electromagnetic radiation. The electromagnetic radiation interacts with the blood and a residual optical signal is both reflected and transmitted by the blood. A photodiode in the light-to-frequency converter (LFC) collects oximetry data from the intravascular blood sample illuminated by the two LEDs. The LFC produces a periodic electrical signal in the form of a pulse train having a frequency, the logarithm of which is in linear relationship to the logarithm of the intensity of the optical signal received by the LFC. The data becomes an input to a high-speed digital counter, which converts the pulsatile signal into a form suitable to be entered into a central processing unit (CPU) of a computer system.

In the alternative, a CPU with an internal counter can be used, thereby eliminating the need for an external counter and further reducing the system size.

Once inside the CPU, the time-domain data is converted into the frequency domain by, for example, performing the well-known Fast Fourier Transform (FFT) on the time-domain data. The frequency domain data is then processed to determine the saturation value.

It is therefore an advantage of the present invention to provide a portable, low-power oximeter.

It is a further object of this invention to provide an improved sensor in the form of a light-to-frequency converter to reduce the parts count of prior art systems.

These and other advantages of the present invention shall become more apparent from a detailed description of the invention.

BRIEF DESCRIPTION OF THE DRAWINGS

In the accompanying drawings, which are incorporated in and constitute a part of this specification, embodiments of the invention are illustrated, which, together with a general description of the invention given above, and the detailed description given below serve to example the principles of this invention.

FIG. 4A is an electrical schematic representation of an implementation of a light-to-frequency converter of the present invention;

FIG. 4B is another embodiment of the LFC shown in FIG. 4A;

FIG. 4C is yet another embodiment of the LFC shown in FIG. 4A; and

FIG. 4D is still another embodiment of the LFC shown in FIG. 4A; and

DETAILED DESCRIPTION OF THE PREFERRED EMBODIMENT

Figure 1:
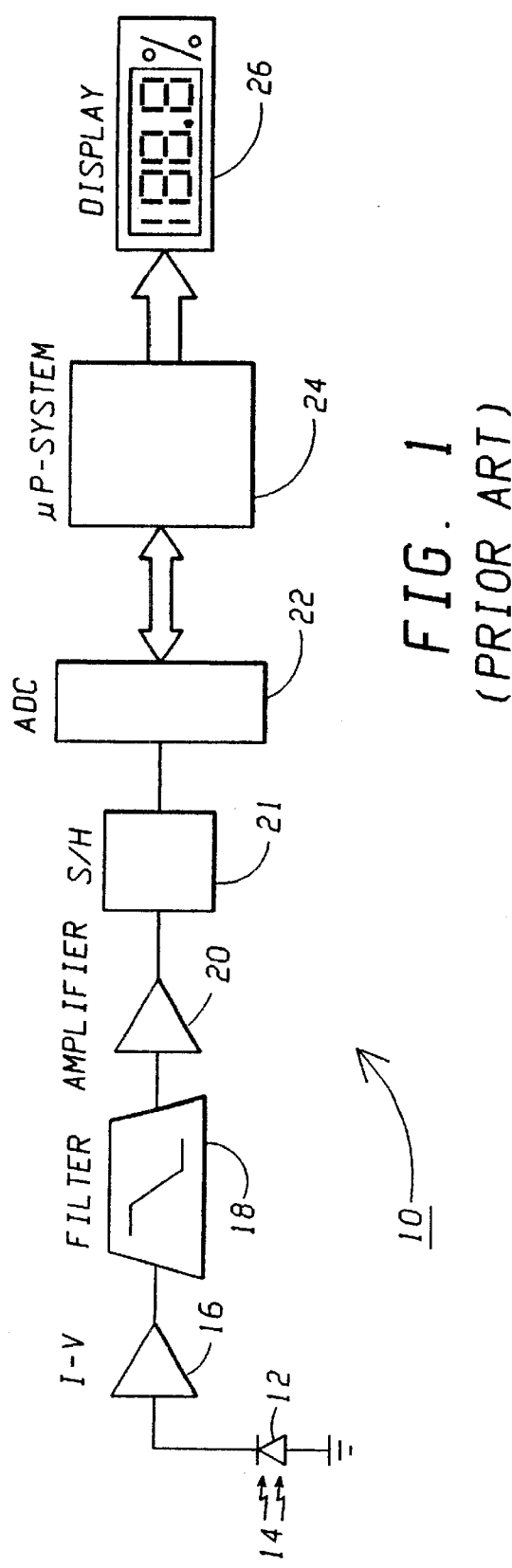
FIG. 1 is an electrical schematic representation of a generic prior art pulse oximeter.

Before describing the details of the present invention, a description of a generic prior art pulse oximeter may be helpful in understanding the advantages of the pulse oximeter of the present invention. Reference is had, therefore, to FIG. 1, which shows a generic prior art pulse oximeter 10. A typical prior art oximeter 10 has a photodiode 12 for detecting an optical signal 14 reflected from or transmitted through a volume of intravascular blood (not shown) illuminated by one or more light emitting diodes (LEDs, not shown). The LEDs emit electromagnetic radiation at a constant intensity; however, an optical signal 14 with a time-varying intensity is transmitted through or reflected back from the intravascular blood for each of the wavelengths. The photodiode 12 generates a low-level current proportional to the intensity of the electromagnetic radiation received by the photodiode 12. The current is converted to a voltage by a current to voltage converter 16, which may be an operational amplifier in a current to voltage (transimpedance) configuration.

The signal is then filtered with a filter stage 18 to remove unwanted frequency components, such as any 60 Hz noise generated by fluorescent lighting. The filtered signal is then amplified with an amplifier 20 and the amplified signal is sampled and held by a sample and hold 21 while the signal is digitized with a high-resolution (12-bit or higher) analog to digital converter (ADC) 22.

The digitized signal is then latched by the CPU (not shown) of the computer system 24 from the ADC 22. The computer system 24 then calculates a coefficient for the oxygen saturation value from the digitized signal and determines the final saturation value by reading the saturation value for the calculated coefficient from a look-up table stored in memory. The final saturation value is displayed on a display 26.

Thus, the generic prior art pulse oximeter 10 requires numerous devices to determine the oxygen saturation value from the optical signal. Moreover, these devices, particularly the ADC 22, require a relatively large amount of space and electrical power, thereby rendering a portable unit impractical.

Under the present invention, the prior art oximeter 10 is modified so that the photodiode 12, current to voltage converter 16, filter 18, amplifier 20, sample and hold 21, and analog-to-voltage converter 22 are replaced with a light-to-frequency converter and a high speed counter.

Figure 2A:
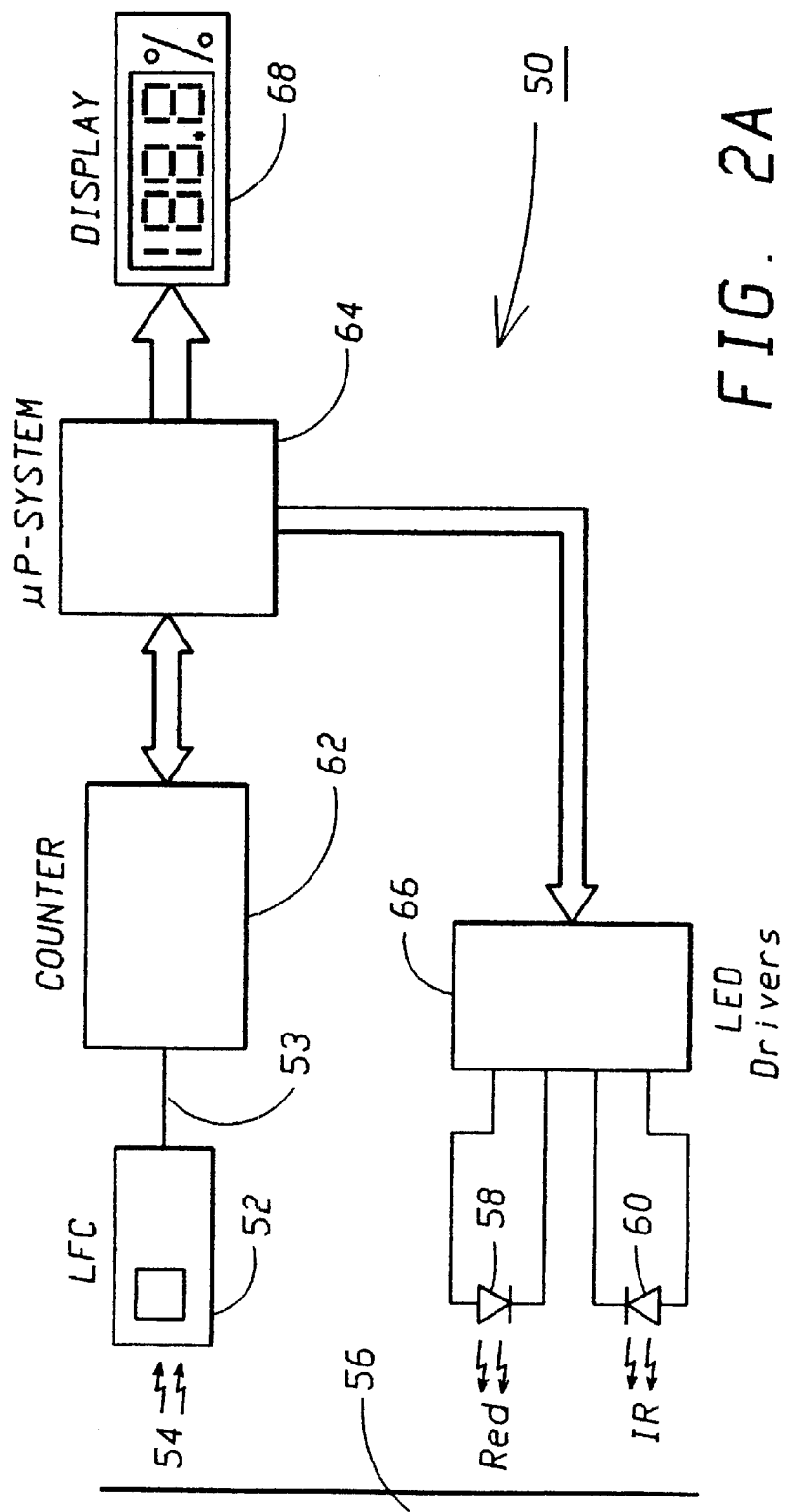
FIG. 2A is an electrical schematic representation of one embodiment of a pulse oximeter of the present invention.

FIG. 2A shows one embodiment of a pulse oximeter 50 of the present invention. The oximeter 50 of the present invention comprises a light-to-frequency converter (LFC) 52 for detecting an optical signal 54 from a volume of intravascular volume of blood 56 illuminated by one or more light emitting diodes (LEDs) 58, 60. The LEDs 58, 60 emit electromagnetic radiation at a constant intensity; however, an optical signal 54 with a time-varying intensity is transmitted through or reflected back by the intravascular blood for each of the wavelengths. In the preferred embodiment, the reflected optical signal 54 is analyzed to determine the saturation value. The LFC 52 produces a periodic electrical signal in the form of a pulse train having a frequency corresponding to the intensity of the broadband optical signal received by the LFC 52. The periodic data then becomes an input to a high-speed digital counter 62, which converts the periodic signal into a form suitable to be entered into a computer system 64.

Once inside the computer system 64, the LFC signal is analyzed to determine the saturation value. In one embodiment, the data is converted into the frequency domain by, for example, performing the well-known Fast Fourier Transform (FFT) on the data. It is also believed that other common techniques of converting time-domain data to the frequency domain will suffice: e.g., discrete cosine transform, wavelet transform, discrete Hartley transform, and Gabor transform. The frequency domain data is then analyzed to determine the saturation value by code executing on the computer system 64, as will be more fully explained in the text accompanying FIG. 4. Once calculated, the saturation value is displayed on a display 68.

In addition to performing saturations calculations, the computer system 64 controls LED drivers 66, which control the LEDs 58, 60.

Figure 2B:
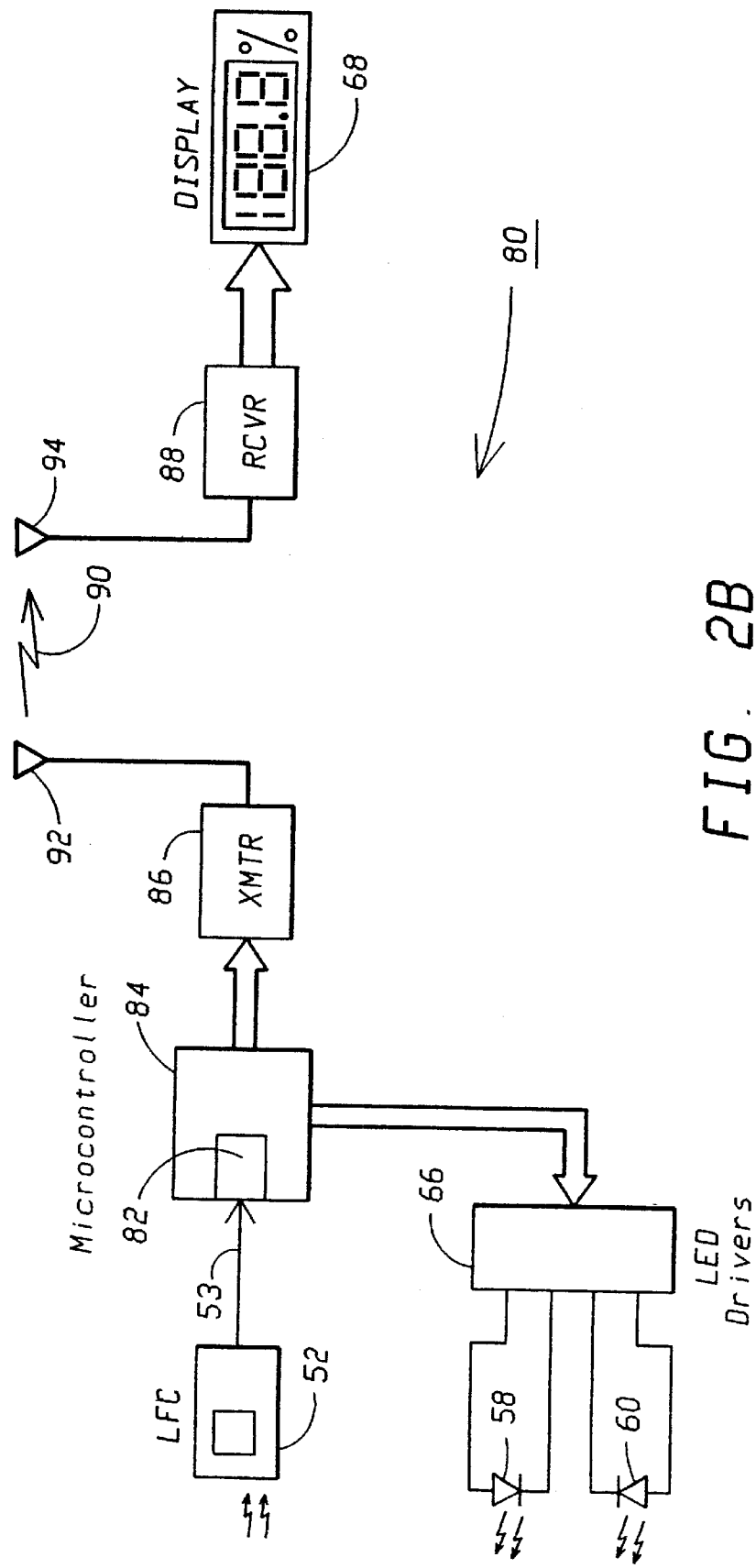
FIG. 2B is an electrical schematic representation of another embodiment of a pulse oximeter of the present invention.

FIG. 2B shows another embodiment of the pulse oximeter of the present invention. The embodiment of FIG. 2B differs from the embodiment in FIG. 2A in two respects. First, the computer system 64 and counter 62 are implemented by a microcontroller 84 having an internal high-speed counter 82 associated therewith. Second, the microcontroller 84 and the display 68 are placed in circuit communication using a transmitter 86 and receiver 88. The transmitter 86 transmits a signal 90 through an antenna 92. The receiver 88 receives the signal 90 through a second antenna 94 and passes the information to the display circuit 68.

Figure 3A:
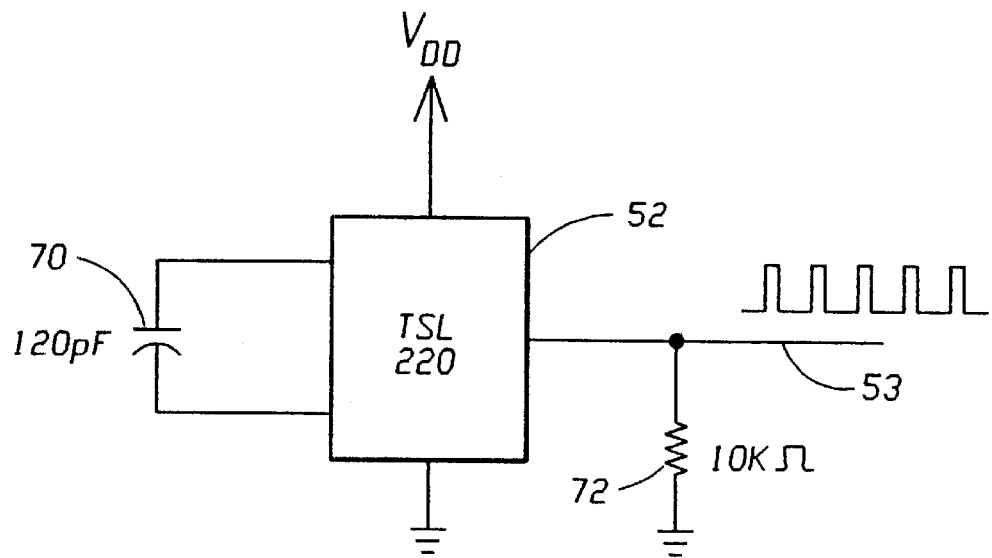
FIG. 3A is an electrical schematic representation of the implementation of the TSL220 light-to-frequency converter in the oximeter of the present invention.
Figure 3B:
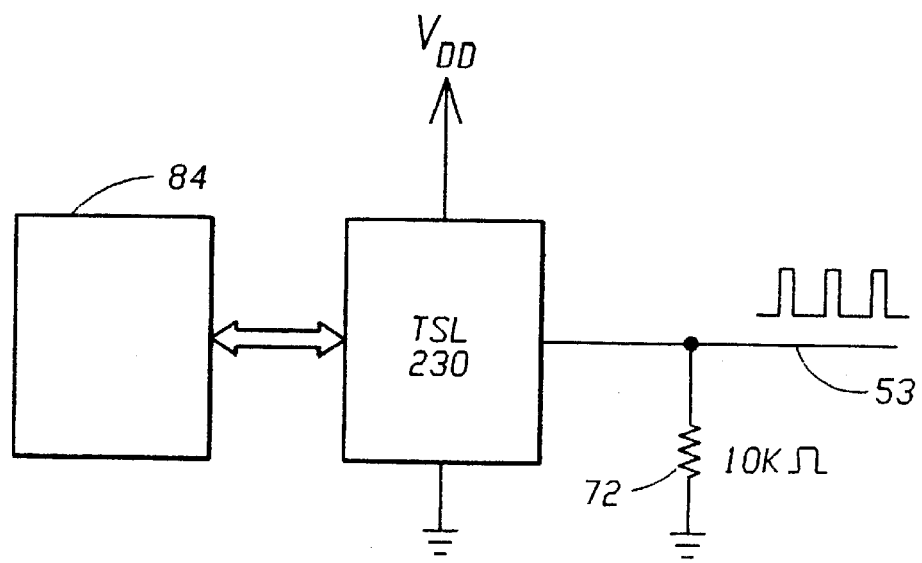
FIG. 3B is an electrical schematic representation of the implementation of the TSL230 light-to-frequency converter in the oximeter of the present invention.

The LFC 52, the counter 62, the computer system 64, the display 68, the LED drivers 66, the LEDs 58, 60, and the other components are connected in electrical circuit communication as shown in FIGS. 2A and 2B. One suitable LFC 52 is the TSL220, manufactured and sold by Texas Instruments, P.O. Box 655303, Dallas, Tex. 75265. FIG. 3A is an electrical schematic representation showing the use of the TSL220 in the oximeter of the present invention. The capacitor 70 and resistor 72 are in circuit communication and have the values as shown in that figure. Another suitable LFC 52 is the TSL230, shown in FIG. 3B, is manufactured by Texas Instruments. Unlike the TSL220, the TSL230 requires no external capacitor and provides microprocessor compatible control lines; therefore, the TSL230 is a one-chip sensor.

Yet another suitable LFC 52 is a novel LFC circuit, which was invented by Stephan Peter Athan, one of the coinventors of this invention, and is shown in FIG. 4A. In that circuit, a photoresistor 73 having a variable resistance is placed in circuit communication with a pulse generating circuit that is configured to generate a periodic electrical signal corresponding to the value of the variable resistance of the photoresistor. In one embodiment, a photoresistor 73, a capacitor 74, and an inverter 75 are placed in circuit communication and have the values shown in that figure. The photoresistor 73 is placed across the input node 76 and the output node 77 of the inverter 73. The capacitor 74 is placed between the input node 76 and ground. The inverter 75 is ideally an inverting Schmitt trigger with hysteresis at its input; however, other inverters are also believed to be suitable.

The photoresistor 73 can be a standard cadmium sulfide or cadmium selenide photoresistor, which are both widely available from many sources. Other types of photoresistors are also available. As is known in the art, the photoresistor 73 has a variable resistance that depends on the amount of electromagnetic radiation 78 being emitted onto the photoresistor. The photoresistor 73, capacitor 74, and inverter 75 are configured such that the period of time in which the capacitor 74 charges and discharges corresponds to the value of the variable resistance of the photoresistor 73. Thus, the output of the inverter 75 is a periodic signal, the period of which depends on the amount of electromagnetic radiation being emitted onto the photoresistor 73.

As shown in FIG. 4B, a resistor 79 with a substantially fixed resistance can be placed in series with the photoresistor 78 and placed across the input 76 and output 77 of the inverter 75. In addition, as shown in FIG. 4C, a multiplying digital to analog converter (MDAC) 80 can be placed in series with the photoresistor 73 and placed across the input 76 and the output 77 of the inverter 75. As shown in that figure, the MDAC 80 is interfaced to the microcontroller 84, which can then control the parameters, and therefore the sensitivity (i.e., shifting the frequency associated with a given amount of illumination to accommodate a broader range of light frequencies), of the circuit by selectively asserting more or less resistance in series with the photoresistor 73. One suitable MDAC is the AD7524 available from Analog Devices, which is essentially a computer controlled R2R network, which is known in the art.

As shown in FIG. 4D, a bank of capacitors with varying capacitance values can be connected in the circuit of FIG. 4A. The capacitors are interfaced to the circuit via a computer controlled bank of analog switches, as shown in that figure. The microcontroller 84 can control the parameters of the circuit, and therefore the sensitivity (i.e., shifting the frequency associated with a given amount of illumination to accommodate a broader range of light frequencies), by selectively connecting one or more of the capacitors to line 76.

While the LFC of FIGS. 4A–4D is believed to be particularly useful in connection with the portable pulse oximeter of the present invention, it is also believed to have utility beyond that of oximetry or other cardiovascular measurement.

Referring back to FIGS. 2A and 2B, the Red LED 58 is a red LED, emitting light having a wavelength of approximately 660 nm. One suitable LED is the P417-ND, which is available from by Digikey, 701 Brooks Avenue South, Thief River Falls, Minn. 56701. It is believed that an LED emitting any wavelength of light in the visible spectrum is suitable; however, because a solution of human hemoglobin has an absorption maximum at a wavelength of about 640 nanometers (red), the closer to that wavelength, the more accurate the results (otherwise, calibration curves are required, as is known in the art).

The IR LED 60 is an infrared LED, emitting electromagnetic radiation having a wavelength of approximately 940 nm. One suitable LED is the F5F1QT-ND, which is also available from Digikey. It is believed that to be suitable, the IR LED 60 must emit electromagnetic radiation at a wavelength such that the absorption of the emitted electromagnetic radiation by the blood 56 is unaffected by the presence or absence of oxygen bound to the hemoglobin molecules.

The counter 62 may be any high speed counter capable of being interfaced to a computer system. One suitable counter is the 4020 CMOS counter, which is manufactured by numerous manufacturers, e.g., Texas Instruments, P.O. Box 655303, Dallas, Tex. 75265, as is well known in the art.

Interfacing the counter 62 to the computer system 64 may be done in several ways. The counter 62 and computer system 64 may be configured to either (1) count the pulses generated by the LFC 52 during a given time period or (2) count the number of pulses of a free-running clock (corresponding to the amount of time) between the individual pulses of the LFC 52. Either method will provide satisfactory data. The latter method can be implemented in several ways. For example, the counter can be reset at each period of the LFC signal. In the alternative, at each edge of LFC pulse train, the value in the counter can be saved to a register and subtracted from the value stored at the previous edge. Either way, the result is a counter value corresponding to the time difference between the two pulse edges. Many configurations are possible. The counter 62 can either count pulses or elapsed time between edges and the computer system 64 either reads the value in the counter periodically by polling the counter, or the computer system 64 reads the value whenever the counter 62 generates an interrupt. Again, many configurations are possible.

The computer system 64 can be any computer system capable of performing oximetry calculations to the desired accuracy in the desired period of time (calculations may be done either in real time or after collection of desired data) and capable of interfacing with a counter 62, a display 68, and LED drivers 66. The computer system 64 may include a CPU, random access memory (RAM), read-only memory (ROM), and associated control circuitry, such as decoders and multi-phase clocks, in circuit communication, as is well known in the art. To be suitable, the computer system must be capable of being a signal analyzer. That is, the computer system 64 must have the computational capacity to determine the saturation value from the periodic pulses.

One suitable computer system 64 is any of several microcontrollers 84, which are known in the art. The 68HC16 microcontroller manufactured by Motorola, Inc., Austin Tex. 78735, is one example. The 68HC16 is suitable for systems requiring low-level digital signal processing and has on-board erasable/programmable ROM (EPROM) and RAM. It also has an on-board 16-bit high-speed counter 82 eliminating the need for an external counter 62. The output from the LFC 52 may be directly connected to the counter input of the 68HC16, thereby allowing the elimination of another discrete device (the separate counter 62). Another suitable microcontroller 84 is the 80CX51FA, which is manufactured by Intel Corp., Santa Clara, Calif. 95051.

If more processing power than either the 68HC16 or the 80CX51FA can provide is, required to determine the saturation value, a digital signal processor or floating point coprocessor (not shown) can be added to the computer system 64. One suitable digital signal processor is the TMS320CX0 digital signal processor, manufactured by Texas Instruments. This device can calculate highly accurate oxygen saturation values in a period of time on the order of microseconds.

The LED drivers 66 may be any driver capable of providing a signal capable of causing one or more LEDs to illuminate. Numerous LED-driving circuits are well known in the art. The drivers 66 must allow the LEDs 58, 60 to be alternatively illuminated under control of the computer system 64.

Some prior art LED drivers have a normalizing function that increases or decreases the intensity of electromagnetic radiation generated by the LEDs in the system. It is desirable to be able use a single oximeter configuration to measure the oxygen saturation of an infant and later to use the same oximeter configuration to measure oxygen saturation levels of an adult. Since the nature of skin and hair of an infant are different from that of an adult, it is generally accepted that an LED intensity calibrated to measure the oxygen saturation level of an adult will be too bright to measure the oxygen saturation level of an infant (the optical signal 54 is so bright that the photodiode saturates). Likewise, it is generally accepted that an LED intensity calibrated to measure saturation of an infant will be too dim to provide adequate data to measure the oxygen saturation of an adult. The normalizing function in some prior art oximeters adjusts the intensities of the LEDs to provide a useful signal under most circumstances.

In the oximeter 50 of the present invention, the normalizing function is not needed. The TSL220 and TSL230 both have 118 Db dynamic ranges. Moreover, the TSL230 has a computer-interfacable gain control for amplification or attenuation of the optical signal, thereby providing an even higher dynamic range. In addition, the LFC of FIG. 4A has a much wider dynamic range. These very wide dynamic ranges allow the use of LED drivers to be configured such that the intensities of the LEDs 58, 60 are set at fixed, predetermined values. The LFCs 52 are so sensitive that an LED intensity suitable for an infant will still generate a reflected optical signal 54 in an adult strong enough to determine the saturation value of that adult. Thus, the LED drivers 66 need not have the ability to normalize the intensities of the LEDs 58, 60.

The display 68 can be any display capable of displaying one or more oxygen saturation values to the desired resolution. Well known displays include seven segment LED displays and liquid crystal displays (LCDs), all of which are well known in the art. In addition, discrete LEDs may be used if the designer desires to display merely a binary oxygen saturation level. For example, green, yellow, and red discrete LEDs can be configured to represent normal, warning, and critical conditions corresponding to saturation values of greater than 90 percent, 80 to 90 percent, and less than 80 percent, respectively.

The transmitter 86, receiver 88, and the two antennas 92, 94 can be any suitable radio frequency or other wireless telemetry system. These telemetry systems are well known in the art and widely available. Additionally, spread spectrum technology provides a highly secure link, a high noise immunity, and a high informational capacity, all of which are desirable in clinical and healthcare environments. A suitable spread spectrum transmitter/receiver pair is believed to be available from Proxim, Mountain View, Calif.

The use of the LFC 52 allows the design of a truly portable pulse oximeter. The TSL230 and the 68HC16 are available in die form (the monolithic electronic device without external packaging or leads), allowing a multichip model (MCM) to be fabricated by connecting the devices at the die-level, as is well known in the art. Display technology for wrist watches and other small devices, also well known in the art, provides a very compact and low-power display 68. LED drivers can comprise surface-mount 2N2222 NPN transistors and surface-mount resistors, both of which are well known in the art and available from numerous sources. Thus, an extremely small pulse oximeter can be constructed according to the principles of the present invention.

Such a pulse oximeter can be light and small enough to be worn by an ambulatory patient. That is, the oximeter can be made light enough and otherwise configured to be worn by a patient in the manner that a wrist watch, bracelet, anklet, inflatable cuff, etc. might be worn.

In addition, telemetry circuits are also available as portable systems from Proxim, Mountain View, Calif., allowing an oximeter to telemeter final oximetry data to the receiver, such as a caregiver's wrist receiver or other type of receiver that communicates the saturation value to a primary caregiver.

In constructing a pulse oximeter according to the present invention, the LEDs 58, 60, the light to frequency converter 52, the counter 62, the microprocessor system 64, and either the display 68 or the transmitter 86 are preferably packaged within a single package. For example, the LEDs 58, 60, LFC 52, microcontroller 84 with internal counter 82, and transmitter 86 can be packaged in a small package about the size and configuration of a wrist watch, with the LEDs 58, 60 and LFC 52 placed in optical communication with the patient's skin. In this example, the antenna 92 can be positioned in a band similar to that of a wrist watch, which can wrap around or otherwise encircle a part of a patient's anatomy (arm, ankle, neck, etc.) to secure the package to the patient, or the antenna 92 can be positioned externally of the package. As another example, the LEDs 58, 60, LFC 52, microcontroller 84 with internal counter 82, and display 68 can be packaged in an inflatable cuff system with the LEDs 58, 60 and LFC 52 placed in optical communication with the patient's skin and the display 68 positioned to be readable by a caregiver. The inflatable cuff can be any of those known in the art, such as those used with blood pressure monitoring equipment.

Virtually any digital pulse oximeter design could be modified to use the LFC 52 of the present invention. Therefore, the invention in its broader aspects is not limited to the specific details, representative apparatus and method, and illustrative examples shown and described. Accordingly, departures may be made from such details without departing from the spirit or scope of the applicant's general inventive concept.

Figure 5:
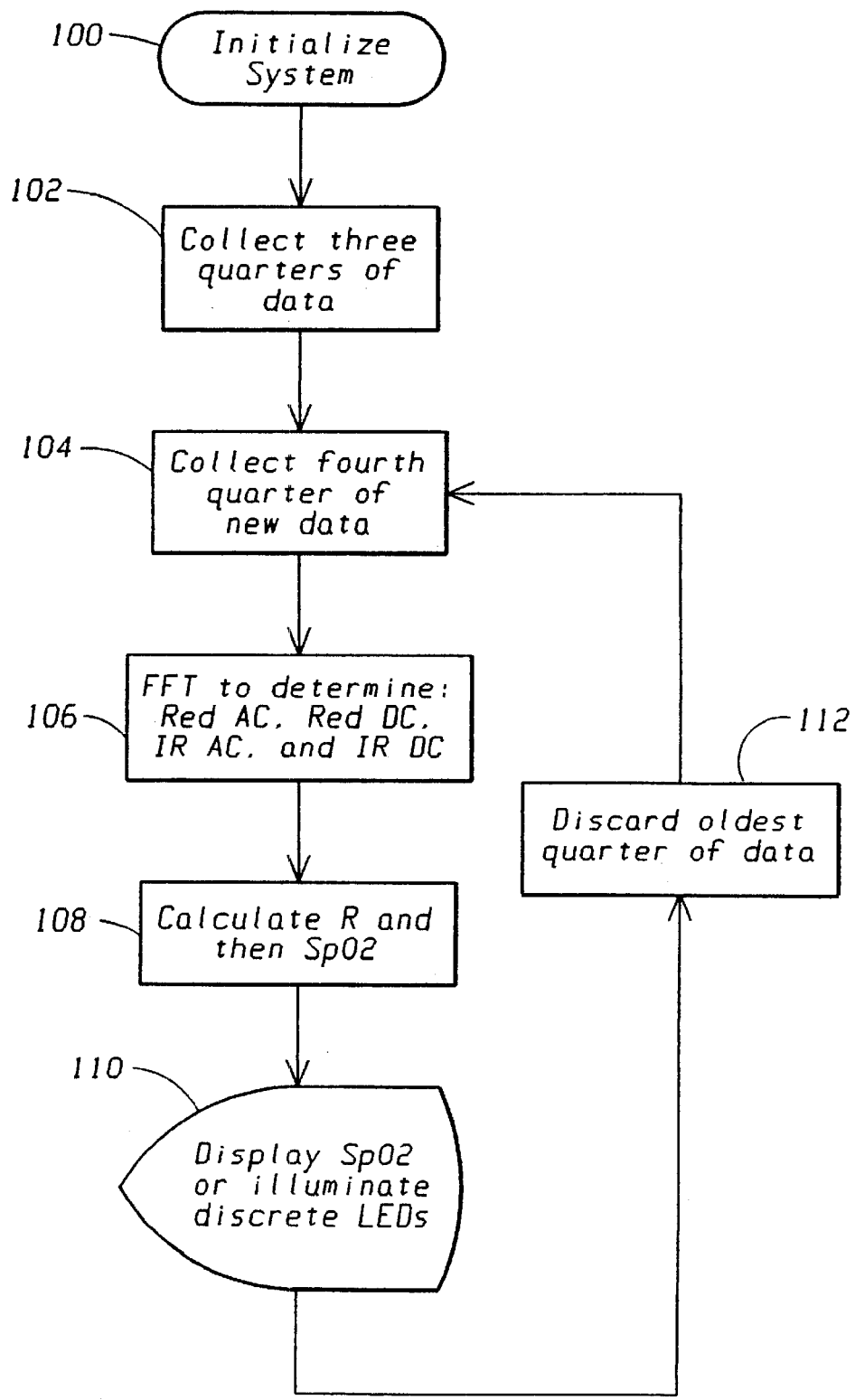
FIG. 5 is a flow chart showing the major process steps taken by the computer system in calculating the saturation value.

FIG. 5 is a flow chart showing the role of the computer system 64 in the pulse oximeter 50 of the present invention.

First, the computer system 64 initializes the system, at 100. Such initialization is very system-specific and is well known in the art. After initializing the system, the computer system 64 begins collecting samples of data. A "sample" is the reading of two intensity values with the LCF 52 and counter 62: (1) an intensity value with the red LED 58 constantly emitting and the infrared LED 60 not emitting and (2) an intensity value with the IR LED 60 constantly emitting and the red LED 58 not emitting.

When either of the LEDs 58, 60 is emitting and a signal 54 is being generated by the interaction of the electromagnetic radiation with the blood 56, the LFC 52 generates a periodic electrical signal in the form of a pulse train with a period corresponding to the intensity of the optical signal 54 received by the LFC 52. This signal is interfaced into the computer system 64 with the counter, as described above, and an intensity value for the red LED 58 and an intensity value for the IR LED 60 are saved in RAM.

Data collection begins at 102. The total collection period is 4.27 seconds in this embodiment, which is divided into four quarters of approximately one second each. As shown at 102, three quarters (approximately three seconds) of data samples are collected to help initialize a sliding window function, described below. Next, the fourth quarter of the total sample (approximately one second worth of samples) is taken, at 104. The sample rate and time of collection are all variable. In this embodiment, between the samples taken at 102 and 104, a total of 4.27 seconds worth of samples are collected for processing. The samples can be taken at many rates, e.g., 15 hertz to 240 Hz, depending on the processing to take place below, as is known in the art.

The system then determines the magnitudes of the AC and DC components for both the Red LED 58 and the IR LED 60 ($AC_{red}$, $DC_{red}$, $AC_{ir}$, and $DC_{ir}$) using a frequency domain analysis, at 106. That is, the 4.27 seconds of time-domain data is then converted into the frequency domain by performing the well-known Fast Fourier Transform (FFT). The FFT can be performed in many ways, as is known in the art. For example, an FFT of between 64 points (on data sampled at 15 Hz) and 1024 points (on data sampled at 240 Hz) will suffice. For both the red and IR signals, the AC component is determined by the magnitude of the highest spectral peak found at from 0.5 to 2.5 Hz and represents the pulsatile, or AC component, of the oximetry waveform. Likewise, the magnitude of the DC component is the highest spectral peak found at from between 0.0 and 0.5 Hz.

Next, at 108, the program calculates an R value from the red and infrared AC and DC spectral peaks, based on the formula: $R=(AC_{red}/DC_{red})/(AC_{ir}/DC_{ir})$ Finally, an $SpO_2$ value is obtained from the approximate formula:

$$SpO_2=-25R+110.$$

These steps were verified using Matlab, which is available from The Mathworks, Inc., Natick, Mass. The formulae applied to the spectral data allowed satisfactory oxygen saturation levels to be calculated. The values were to within 2% (one standard deviation) of correct oxygen saturation levels, as measured by an IL-282 Cooximeter for the waveforms analyzed, which is adequate for commercial use.

As is known, in the alternative to the FFT, many other methods can be used to determine the AC and DC components. For example, the well known discrete cosine transform, wavelet transform, discrete Hartley transform, and Gabor transform can all be used.

Next, the calculated saturation value is displayed on the display 68, as is well known in the art, at 110.

Finally, the program loops back to 104, where another one quarter of 4.27 seconds of data is collected. As indicated at 112, the oldest quarter of data is discarded so that 4.27 seconds of data remain (only approximately one second of which is new). Thus a 4.27 second window of data can be thought of as sliding by one-quarter increments, thereby discarding approximately one second of data and sampling a new one second of data. The steps at 104, 106, 108, 110, and 112 are performed repeatedly, thereby displaying a new $SpO_2$ value approximately each second.

While the present invention has been illustrated by the description of embodiments thereof, and while the embodiments have been described in considerable detail, it is not the intention of the applicant to restrict or in any way limit the scope of the appended claims to such detail. Additional advantages and modifications will readily appear to those skilled in the art. For example, other light-to-frequency converters can be used. As another example, a 2048-point FFT can be performed on 8.53 seconds of data collected at 240 Hz. Finally, with minor modifications to the signal analysis portion of this system, the present invention can be used as a diagnostic instrument for determining other cardiovascular system parameters, such as pulse rate, respiration rate, and intravascular volume status. Therefore, the invention in its broader aspects is not limited to the specific details, representative apparatus and method, and illustrative examples shown and described. Accordingly, departures may be made from such details without departing from the spirit or scope of the applicant's general inventive concept.

We claim:

1. A diagnostic probe for measuring a parameter of a cardiovascular system comprising:

an electromagnetic radiation source for illumination of a volume of intravascular blood with electromagnetic radiation, the electromagnetic radiation having at least one frequency component having an intensity, the intensity of the at least one frequency component of the electromagnetic radiation being altered by interaction with the volume of intravascular blood thereby generating an optical signal from the interaction of the at least one frequency component of the electromagnetic radiation with the volume of intravascular blood, the optical signal having an intensity; and a light-to-frequency converter having an electromagnetic radiation sensor electrically connected to an electronic signal generator, said electromagnetic radiation sensor being optically coupled to said electromagnetic radiation source for reception of the optical signal and said electronic signal generator generating a periodic electrical signal responsive to said electromagnetic radiation sensor, the periodic electrical signal comprising a digital pulse train having pulses, the timing of the pulses of the electrical signal corresponding to the intensity of the optical signal.

2. A diagnostic probe according to claim 1 further comprising an inflatable cuff associated with said electromagnetic radiation source and wherein said electromagnetic radiation source is placed in optical communication with a patient's skin associated with the volume of intravascular blood.

3. A pulse oximeter probe comprising:

an electromagnetic radiation source for illumination of a volume of intravascular blood with electromagnetic radiation, the volume of intravascular blood having an oxygen saturation level of hemoglobin within the volume of blood, the electromagnetic radiation having at least one frequency component having an intensity, the intensity of the at least one frequency component of the electromagnetic radiation being altered by interaction with oxyhemoglobin in the volume of intravascular blood thereby generating an optical signal from the interaction of the at least one frequency component of the electromagnetic radiation with the oxyhemoglobin in the volume of intravascular blood, the optical signal having an intensity; and a light-to-frequency converter having an electromagnetic radiation sensor electrically connected to an electronic signal generator, said electromagnetic radiation sensor being optically coupled to said electromagnetic radiation source for reception of the optical signal and said electronic signal generator generating a periodic electrical signal responsive to said electromagnetic radiation sensor, the periodic electrical signal comprising a digital pulse train having pulses, the timing of the pulses of the electrical signal corresponding to the intensity of the optical signal.

4. A pulse oximeter probe according to claim 3 wherein a value associated with the intensity of the optical signal received by said electromagnetic radiation sensor has a logarithm, the periodic electrical signal generated by said electronic signal generator of said light-to-frequency converter has a frequency, a value associated with the frequency has a logarithm, and the logarithm of the value associated with the frequency is in linear relationship to the logarithm of the value associated with the intensity of the optical signal received by said electromagnetic radiation sensor of said light-to-frequency converter.

5. A pulse oximeter probe according to claim 3 wherein said electromagnetic radiation source comprises a first emitter of electromagnetic radiation for selectively illuminating the intravascular blood with electromagnetic radiation of a first frequency and a second emitter of electromagnetic radiation for selectively illuminating the intravascular blood with electromagnetic radiation of a second frequency;

wherein electromagnetic radiation at said second frequency has an absorption coefficient with respect to oxyhemoglobin; and wherein electromagnetic radiation at said first frequency has an absorption coefficient with respect to oxyhemoglobin that is substantially different than the absorption coefficient with respect to hemoglobin of electromagnetic radiation at said second frequency.

6. A pulse oximeter according to claim 5 further comprising an inflatable cuff associated with said electromagnetic radiation source and wherein said electromagnetic radiation source is placed in optical communication with a patient's skin associated with the volume of intravascular blood.

7. A pulse oximeter according to claim 3 further comprising an inflatable cuff associated with said electromagnetic radiation source and wherein said electromagnetic radiation source is placed in optical communication with a patient's skin associated with the volume of intravascular blood.

8. A diagnostic instrument probe for determining a parameter of a cardiovascular system comprising:

an electromagnetic radiation source for illumination of a volume of intravascular blood with electromagnetic radiation, the electromagnetic radiation having at least one frequency component having an intensity, the intensity of the at least one frequency component of the electromagnetic radiation being altered by interaction with the volume of intravascular blood thereby generating an optical signal from the interaction of the at least one frequency component of the electromagnetic radiation with the volume of intravascular blood, the optical signal having an intensity; and a light-to-frequency converter having an electromagnetic radiation sensor electrically connected to an electronic signal generator, said electromagnetic radiation sensor being optically coupled to said electromagnetic radiation source for reception of the optical signal and said electronic signal generator generating a periodic electrical signal responsive to said electromagnetic radiation sensor, the periodic electrical signal comprising a digital pulse train having pulses, the timing of the pulses of the electrical signal corresponding to the intensity of the optical signal.

9. A diagnostic instrument probe according to claim 8 wherein said inverting circuit has an input and an output and wherein said photoresistor is electrically connected in a feedback path between said output and said input of said inverting circuit.

10. A diagnostic instrument probe according to claim 8 further comprising an additional resistive device, wherein said inverting circuit has an input and an output, and wherein said photoresistor is electrically connected in series relation with the additional resistive device in a feedback path between said output and said input of said inverting circuit.

11. A diagnostic instrument probe according to claim 8 wherein said inverting circuit has an input and an output and wherein the digital pulse train of the periodic electrical signal is generated at said output of said inverting circuit.

12. A diagnostic instrument probe according to claim 8 further comprising an inflatable cuff associated with said electromagnetic radiation source and wherein said electromagnetic radiation source is placed in optical communication with a patients skin associated with the volume of intravascular blood.

13. A pulse oximeter probe comprising:

an electromagnetic radiation source for illumination of a volume of intravascular blood with electromagnetic radiation, the volume of intravascular blood having an oxygen saturation level of hemoglobin within the volume of blood, the electromagnetic radiation having at least one frequency component having an intensity, the intensity of the at least one frequency component of the electromagnetic radiation being altered by interaction with oxyhemoglobin in the volume of intravascular blood thereby generating an optical signal from the interaction of the at least one frequency component of the electromagnetic radiation with the oxyhemoglobin in the volume of intravascular blood, the optical signal having an intensity; and a light-to-frequency converter having an electromagnetic radiation sensor electrically connected to an electronic signal generator, said electromagnetic radiation sensor being optically coupled to said electromagnetic radiation source for reception of the optical signal and said electronic signal generator generating a periodic electrical signal responsive to said electromagnetic radiation sensor, the periodic electrical signal comprising a digital pulse train having pulses, the timing of the pulses of the electrical signal corresponding to the intensity of the optical signal;

wherein said electromagnetic radiation sensor comprises a photoresistor having a resistance, the resistance being variable and corresponding to an amount of electromagnetic radiation illuminating said photoresistor;

wherein said electronic signal generator comprises an inverting circuit electrically connected to a capacitor;

wherein said capacitor charges and discharges over a period of time responsive to said inverting circuit and said photoresistor; and wherein the period of time in which said capacitor charges and discharges corresponds to the resistance of said photoresistor.

14. A pulse oximeter probe according to claim 13 wherein said inverting circuit has an input and an output and wherein said photoresistor is electrically connected in a feedback path between said output and said input of said inverting circuit.

15. A pulse oximeter probe according to claim 13 further comprising an additional resistive device, wherein said inverting circuit has an input and an output, and wherein said photoresistor is electrically connected in series relation with the additional resistive device in a feedback path between said output and said input of said inverting circuit.

16. A pulse oximeter probe according to claim 13 wherein said inverting circuit has an input and an output and wherein the digital pulse train of the periodic electrical signal is generated at said output of said inverting circuit.

17. A pulse oximeter probe according to claim 13 further comprising an inflatable cuff associated with said electromagnetic radiation source and wherein said electromagnetic radiation source is placed in optical communication with a patient's skin associated with the volume of intravascular blood.

18. A diagnostic instrument probe for measuring a parameter of a cardiovascular system comprising:

an electromagnetic radiation source for illumination of a volume of intravascular blood with electromagnetic radiation, the electromagnetic radiation having at least one frequency component having an intensity, the intensity of the at least one frequency component of the electromagnetic radiation being altered by interaction with the volume of intravascular blood thereby generating an optical signal from the interaction of the at least one frequency component of the electromagnetic radiation with the volume of intravascular blood, the optical signal having an intensity;

a light-to-frequency converter having an electromagnetic radiation sensor electrically connected to an electronic signal generator, said electromagnetic radiation sensor being optically coupled to said electromagnetic radiation source for reception of the optical signal and said electronic signal generator generating a periodic electrical signal responsive to said electromagnetic radiation sensor, the periodic electrical signal comprising a digital pulse train having pulses, the timing of the pulses of the electrical signal corresponding to the intensity of the optical signal; and a transmitter for wirelessly communicating to a remote receiver a signal corresponding to the measured cardiovascular system parameter.

19. A pulse oximeter probe comprising:

an electromagnetic radiation source for illumination of a volume of intravascular blood with electromagnetic radiation, the volume of intravascular blood having an oxygen saturation level of hemoglobin within the volume of blood, the electromagnetic radiation having at least one frequency component having an intensity, the intensity of the at least one frequency component of the electromagnetic radiation being altered by interaction with oxyhemoglobin in the volume of intravascular blood thereby generating an optical signal from the interaction of the at least one frequency component of the electromagnetic radiation with the oxyhemoglobin in the volume of intravascular blood, the optical signal having an intensity;

a light-to-frequency converter having an electromagnetic radiation sensor electrically connected to an electronic signal generator, said electromagnetic radiation sensor being optically coupled to said electromagnetic radiation source for reception of the optical signal and said electronic signal generator generating a periodic electrical signal responsive to said electromagnetic radiation sensor, the periodic electrical signal comprising a digital pulse train having pulses, the timing of the pulses of the electrical signal corresponding to the intensity of the optical signal; and a transmitter for wirelessly communicating to a remote receiver a signal corresponding to the measured oxygen saturation level of the hemoglobin within the volume of blood.

20. A probe for use in measuring a pulse rate of a cardiovascular system comprising:

an electromagnetic radiation source for illumination of a volume of intravascular blood with electromagnetic radiation, the electromagnetic radiation having at least one frequency component having an intensity, the intensity of the at least one frequency component of the electromagnetic radiation being altered by interaction with the volume of intravascular blood thereby generating an optical signal from the interaction of the at least one frequency component of the electromagnetic radiation with the volume of intravascular blood, the optical signal having an intensity; and a light-to frequency converter having an electromagnetic radiation sensor electrically connected to an electronic signal generator, said electromagnetic radiation sensor being optically coupled to said electromagnetic radiation source for reception of the optical signal and said electronic signal generator generating a periodic electrical signal responsive to said electromagnetic radiation sensor, the periodic electrical signal comprising a digital pulse train having pulses, the timing of the pulses of the electrical signal corresponding to the intensity of the optical signal.

21. A probe for use in measuring a pulse rate of a cardiovascular system according to claim 20 further comprising a transmitter for transmitting to a remote receiver a signal corresponding to the pulse rate of the cardiovascular system.

22. A probe for use in measuring a respiration rate of a cardiovascular system comprising:

an electromagnetic radiation source for illumination of a volume of intravascular blood with electromagnetic radiation, the electromagnetic radiation having at least one frequency component having an intensity, the intensity of the at least one frequency component of the electromagnetic radiation being altered by interaction with the volume of intravascular blood thereby generating an optical signal from the interaction of the at least one frequency component of the electromagnetic radiation with the volume of intravascular blood, the optical signal having an intensity; and a light-to-frequency converter having an electromagnetic radiation sensor electrically connected to an electronic signal generator, said electromagnetic radiation sensor being optically coupled to said electromagnetic radiation source for reception of the optical signal and said electronic signal generator generating a periodic electrical signal responsive to said electromagnetic radiation sensor, the periodic electrical signal comprising a digital pulse train having pulses, the timing of the pulses of the electrical signal corresponding to the intensity of the optical signal.

23. A probe for use in measuring a respiration rate of a cardiovascular system according to claim 22, further comprising a transmitter for transmitting to a remote receiver a signal corresponding to the respiration rate of the cardiovascular system.

24. A probe for use in measuring an intravascular volume status of a cardiovascular system comprising:

an electromagnetic radiation source for illumination of a volume of intravascular blood with electromagnetic radiation, the electromagnetic radiation having at least one frequency component having an intensity, the intensity of the at least one frequency component of the electromagnetic radiation being altered by interaction with the volume of intravascular blood thereby generating an optical signal from the interaction of the at least one frequency component of the electromagnetic radiation with the volume of intravascular blood, the optical signal having an intensity; and a light-to-frequency converter having an electromagnetic radiation sensor electrically connected to an electronic signal generator, said electromagnetic radiation sensor being optically coupled to said electromagnetic radiation source for reception of the optical signal and said electronic signal generator generating a periodic electrical signal responsive to said electromagnetic radiation sensor, the periodic electrical signal comprising a digital pulse train having pulses, the timing of the pulses of the electrical signal corresponding to the intensity of the optical signal.

25. A probe for use in meansuring an intravascular volume status of a cardiovascular system according to claim 24, further comprising a transmitter for transmitting to a remote receiver a signal corresponding to the intravascular volume status of the cardiovascular system.

26. A method of producing a periodic electrical signal indicative of a parameter of a cardiovascular system comprising:

illuminating a volume of intravascular blood with electromagnetic radiation, the electromagnetic radiation having at least one frequency component having an intensity, the intensity of the at least one frequency component of the electromagnetic radiation being altered by interaction with the volume of intravascular blood thereby generating an optical signal from the interaction of the at least one frequency component of the electromagnetic radiation with the volume of intravascular blood, the optical signal having an intensity;

optically coupling a light-to-frequency converter to receive the optical signal; and generating with the light-to-frequency converter the periodic electrical signal comprising a digital pulse train having pulses, the timing of the pulses of the electrical signal corresponding to a parameter of the optical signal.

\* \* \* \* \*

UNITED STATES PATENT AND TRADEMARK OFFICE
CERTIFICATE OF CORRECTION

PATENT NO. : 6,496,711 B1
DATED : December 17, 2002
INVENTOR(S) : Stephan Peter Athan, John Edward Scharf It is certified that error appears in the above-identified patent and that said Letters Patent is hereby corrected as shown below:

<u>Column 13,</u>
Line 63, replace "patients" with -- patient's --.

Signed and Sealed this

First Day of July, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,496,711 B1
DATED : December 17, 2002
INVENTOR(S) : Stephan Peter Athan and John Edward Scharf It is certified that error appears in the above-identified patent and that said Letters Patent is hereby corrected as shown below:

<u>Title page,</u>
Item [73], Assignee, replace "University of Florida, Tampa, FL (US)" with
-- University of South Florida, Tampa, FL (US) --.

Signed and Sealed this

Seventeenth Day of February, 2004

JON W. DUDAS
*Acting Director of the United States Patent and Trademark Office*